Feb. 2, 1965 W. E. SILVA Plant Pat. 2,469
BLACKBERRY PLANT
Filed Aug. 27, 1963
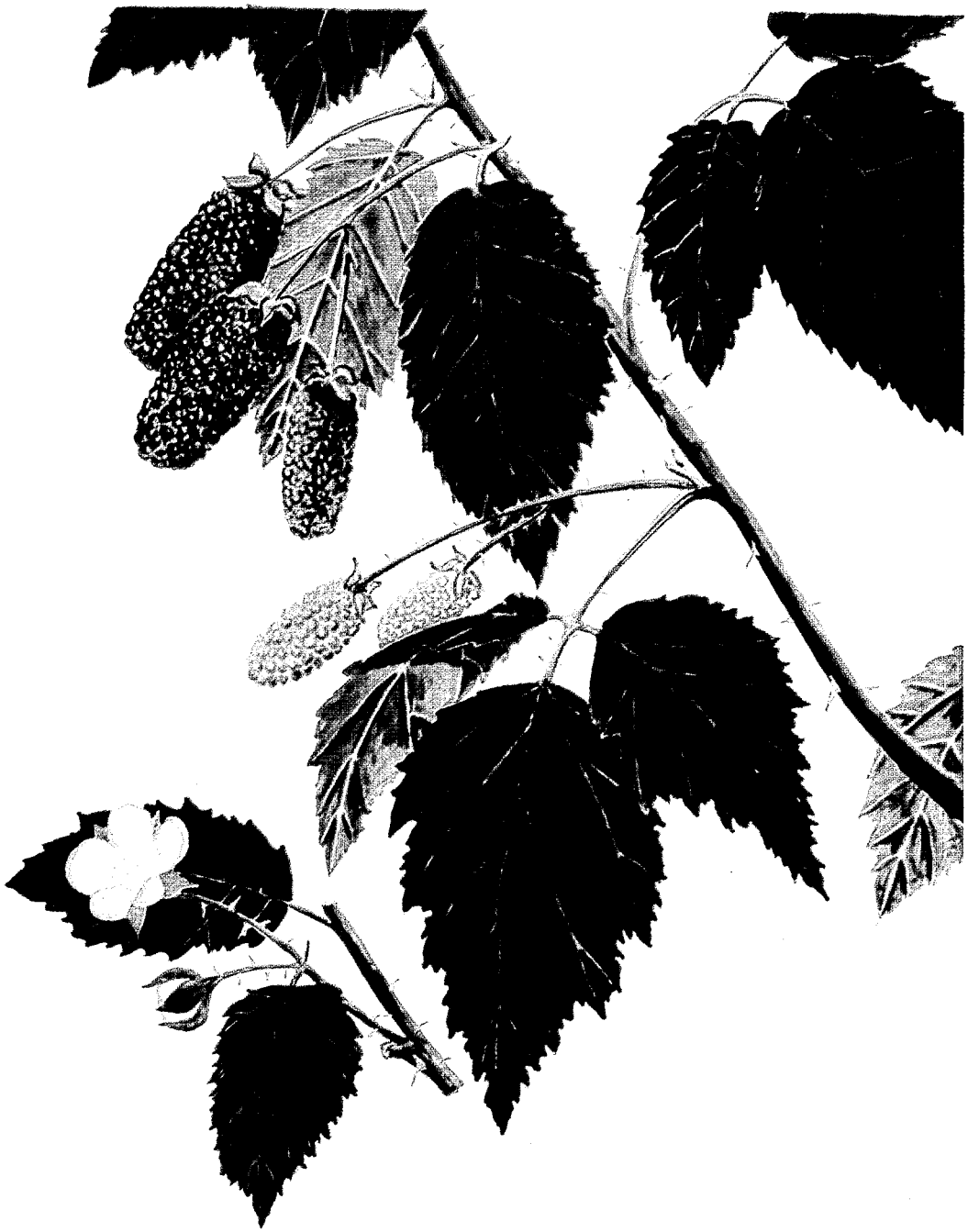
WITNESS
Samuel H. Grow
INVENTOR
WILLIAM E. SILVA
by Rummler & Grow
ATTYS.

United States Patent Office

Plant Pat. 2,469
Patented Feb. 2, 1965

2,469
BLACKBERRY PLANT

William E. Silva, 408 Water Trough Road, Sebastopol, Calif.

Filed Aug. 27, 1963, Ser. No. 305,021
1 Claim. (Cl. Plt.—46)

My present disclosure concerns an improved blackberry plant which I have developed in the course of extensive breeding efforts carried on by me in my nursery at Sebastopol, California with the object of producing an improved blackberry plant with strong disease resistance, particularly for leaf spot and cane blight and which would be a heavy producer of berries that will not burn or scald and which will be tasty, clean and firm, with good shipping qualities for commercial purposes.

My new variety of blackberry plant resulted as a seedling of the variety "Mammoth" (unpatented) with the variety "Crandall" (unpatented) as the pollen parent, and was observed by me to have the best qualities of its parents, insofar as vigorous, disease free growth and shape and size of fruit are concerned, as well as the added advantages of a heavy production of firm berries with all berries being of a uniformly large size and ripening completely, on the bush, in one season so that practically no berries are lost when harvesting the crop. Asexual reproduction of this new variety under my direction, by means of late winter tips, at Sebastopol, California has proved its advantageous characteristics to be fixed and to remain true in successive generations.

The accompanying drawings, in color, illustrate the distinctive character of the fruit of my new blackberry plant, the nature of its foliage and, in the separate figure at the lower left, the bud and blossom, the colors shown being substantially true.

My new variety of blackberry plant is generally of bush form and is a climber like its parent "Mammoth." The plant has 9 to 12 canes, each approximately 1 inch in diameter at the base, and its runners are generally from 12 to 18 feet long, with the fruiting spurs, 4 to 7 inches long, occurring over the entire length from the base of the plant to the end of the runner.

The foliage of the new plant is large and heavy, somewhat like that of its parent "Crandall." The mature leaf usually comprises an odd-pinnate arrangement of 3 ovate, irregularly serrated, leaflets on a peduncle that is 1½ to 2 inches long; and the center leaflet of the mature leaf is about 3½ inches long and about 2½ inches wide. The runners have closely spaced heavy thorns 3/32 to 5/32 inch long and the peduncles and the mid-ribs of the leaflets have small irregularly spaced prickles.

The blossom period for my new variety, in the Sebastopol, California region, is from June 1st to about the 18th. The buds are globular and usually about ⅜ inch in diameter and about ¼ inch high, with a 5 lobed funnel shaped calyx. The flowers are about ⅞ to 1 inch in diameter when fully opened and have 5 petals.

The plant is fruit bearing within 2 years from start as a late winter cane tip and the fruiting season is from about June 20 to the end of July, in the Sebastopol area, with 6 to 8 berries being produced on each spur. The berries, when ripe, are about 1⅜ to 1¾ inches long and approximately ⅝ inch in diameter. The berries are very firm, generally cylindrical in shape and have from 85 to 90 drupelets. The flavor of the berries is very good and the aroma is prominent. The berries are sub-acid, but have somewhat more acidity than the berries of either parent, and test to 12.3 percent in total solids.

Also, the new variety withstands below-freezing weather without apparent harm and in rainy, wet weather the plant develops with a luxuriant growth, producing heavy vines. The ripe berries will not dry on the vine and will hold up and stay firm for 8 days or more, thus permitting time for all the fruit to ripen and a harvest with maximum production of shipping fruit.

The color characteristics of my new variety of blackberry plant, according to "A Dictionary of Color" by Maerz and Paul, are as follows:

| | Plate | Letter | Number |
|---|---|---|---|
| Leaves: | | | |
| Mature Leaf—face side | 23 | J | 9 to 10 |
| Mature Leaf—under side | 21 | L | 5 |
| Veins—face of leaf | 19 | L | 5 |
| Veins—under side | 19 | E | 1 |
| Stems: | | | |
| Basic color of all stems | 21 | L | 1 to 4 |
| Red tone on upper side of stems | 5 | L | 10 to 12 |
| Fruit: | | | |
| Mature fruit | 55 | H | 11 |
| Maturing fruit | 53 | L | 9 to 12 |
| Immature fruit | 19 | I | 6 |
| Flower: | | | |
| Petals—top side | 17 | B | 1 |
| Stamens | 17 | K | 1 |
| Sepals | 21 | L | 1 |
| Thorns: | | | |
| Base of thorn | 21 | B | 1 |
| Tip of thorn | 5 | L | 10 |

In general my new variety of blackberry plant appears much like the variety "Mammoth" or "Olallie" except that the berries are longer and substantially cylindrical in form. Also, the berries are much more firm and, unlike "Mammoth," the ripe berries can be shipped commercially over great distances. The new variety is a much heavier producer of fruit than either of its parents because of its spur system of growth and its berries do not burn because of the heavy foliage and strong growing nature of the plant. The new plant has exhibited no sign of the usual leaf spot and cane blight diseases and appears to be fully free of root canker or anthracnose. Also, the new variety has exhibited the strong hybrid vigor of its parent "Crandall," which is known to be a disease free plant, and hence the berry production is very heavy with no loss from fungus which would injure the crop. A particular distinction of the new variety with respect to the variety "Olallie" is that the latter starts bearing fruit about one and one-half to two weeks earlier and its berries are very soft, ripening all at once within one and one-half weeks or less, whereas with the new variety the berries remain firm for more than a week after ripening and the ripening period extends for a relatively long time.

Having now described and illustrated my new variety of blackberry plant, I claim:

A new and distinct variety of blackberry plant, substantially as herein shown and described, particularly characterized by its large, generally cylindrical and very firm berries, its heavy rate of berry production with all berries ripening on the plant during one season, and its freedom from leaf spot and cane blight.

No references cited.

ABRAHAM G. STONE, *Primary Examiner.*